United States Patent [19]
Nelson et al.

[11] Patent Number: 5,772,854
[45] Date of Patent: *Jun. 30, 1998

[54] USE OF PAIRED REBOILERS IN THE PURIFICATION OF PROPYLENE OXIDE BY EXTRACTIVE DISTILLATION

[75] Inventors: William Pleasant Nelson, Nederland; Mark Elliott Taylor, Orange, both of Tex.

[73] Assignee: Huntsman Specialty Chemicals Corporation, Austin, Tex.

[ * ] Notice: The term of this patent shall not extend beyond the expiration date of Pat. No. 5,453,160.

[21] Appl. No.: 516,374

[22] Filed: Aug. 17, 1995

[51] Int. Cl.⁶ ............................ B01D 3/40; C07D 301/32
[52] U.S. Cl. .................... 203/64; 203/78; 203/80; 203/DIG. 9; 203/DIG. 25; 549/541
[58] Field of Search ............................. 203/64, DIG. 25, 203/71, 14, 78, 80, DIG. 9; 549/541

[56] References Cited

U.S. PATENT DOCUMENTS

| | | | |
|---|---|---|---|
| 4,248,672 | 2/1981 | Smith | 203/81 |
| 4,690,733 | 9/1987 | Forte et al. | 203/DIG. 25 |
| 4,778,567 | 10/1988 | Kakimoto et al. | 203/DIG. 25 |
| 4,874,475 | 10/1989 | McLaughlin et al. | 203/DIG. 25 |
| 4,971,661 | 11/1990 | Meyer et al. | 203/80 |
| 5,238,540 | 8/1993 | Skatulla et al. | 203/DIG. 19 |
| 5,453,160 | 9/1995 | Peters et al. | 203/DIG. 9 |
| 5,464,505 | 11/1995 | Peters et al. | 203/64 |
| 5,489,366 | 2/1996 | Jongenburger | 203/80 |

*Primary Examiner*—Virginia Manoharan
*Attorney, Agent, or Firm*—Russell R. Stolle; Carl G. Ries

[57] ABSTRACT

In the purification of an aqueous acetone-contaminated propylene oxide feedstock in an extractive distillation column in the presence of an oxyalkylene glycol extractive distillation agent under distillation conditions selected to promote the formation and maintenance of an acetone buffer in the distillation column, a higher boiling (heavier) distillation fraction containing substantially all of the oxyalkylene glycols, water, and acetone introduced into the extractive distillation column is continuously withdrawn and the higher boiling (heavier) distillation fraction is partially vaporized in a first reboiler; the remaining liquid being partially vaporized in a second reboiler and the vapors being recycled to the extractive distillation column.

16 Claims, 2 Drawing Sheets

USE OF PAIRED REBOILERS IN THE PURIFICATION OF PROPYLENE OXIDE BY EXTRACTIVE DISTILLATION

BACKGROUND OF THE INVENTION

1. Technical Field of the Invention

This invention relates to the continuous purification of propylene oxide. More particularly, this invention relates to a distillation process for continuously removing contaminating quantities of impurities including oxygen-containing impurities such as methanol, acetone and water from an impure propylene oxide feedstock. Still more particularly, this invention relates to a method for the extractive distillation of an impure propylene oxide feedstock, such as a feedstock contaminated with from about 50 to about 4,000 ppm of methanol, from about 0.01 to about 2 wt. % of water and from about 0.01 to about 2 wt. % of acetone using an oxyalkylene glycol extractive distillation agent wherein the impure propylene oxide is distilled under conditions of predetermined temperature and pressure selected to promote the formation and maintenance of an acetone buffer zone, wherein a heavier distillation fraction containing substantially all of the oxyalkylene glycols, water, acetone and methanol is withdrawn adjacent the bottom of the distillation column, and passed to a first reboiler, and heated therein to partially vaporize the heavier distillation fraction to provide a first vaporized reboiler fraction rich in acetone and lean in oxyalkylene glycols, wherein the unvaporized liquid portion of the heavier distillation fraction is passed to a second reboiler and heated therein to further partially vaporize the unvaporized liquid portion to provide a second vaporized reboiler fraction lean in acetone and rich in oxyalkylene glycols, and wherein the first and said second vaporized recycle fractions are recycled to the extractive distillation column at a point below the acetone buffer zone.

2. Prior Art a. General Background Information

It is known to react a hydroperoxide feedstock such as tertiary butyl hydroperoxide with propylene in the presence of an epoxidation catalyst in order to provide a reaction product comprising propylene oxide, an alcohol corresponding to the hydroperoxide feedstock, a solvent, and impurities (see, for example, Kollar U.S. Pat. No. 3,350,422, Kollar U.S. Pat. No. 3,351,635 and Sorgenti U.S. Pat. No. 3,666,777.

It is also known to separate the reaction product by distillation in order to obtain a plurality of fractions including, for example, a propylene recycle fraction, a propylene oxide product fraction, an alcohol fraction, etc.

It is also known that methanol, acetone and water are common contaminants for propylene oxide which are removed only with difficulty.

For example, Mitchell et al. U.S. Pat. No. 2,550,847 is directed to a process for separating purified propylene oxide from a crude propylene oxide product contaminated with acetaldehyde, methyl formate, methanol, etc., by treating the crude mixture with an aqueous basic substance followed by recovery of the purified propylene oxide by any suitable means such as by decantation. Mitchell et al. reported a recovery of a product containing 78 to 82 wt. % of propylene oxide which, they stated, could be increased in purity to about 95 to 99% by fractional distillation.

b. Extractive Distillation Background

Burns et al. U.S. Pat. No. 3,715,284 discloses a process for the purification of impure propylene oxide using acetone or a mixture of acetone with methanol which is introduced into a distillation column either below or together with the impure propylene oxide.

Schmidt U.S. Pat. No. 4,140,588 discloses a process for the purification of propylene oxide contaminated with methanol and acetone using water as an extractive distillation agent, the water being introduced into the distillation column above the point of introduction of the crude propylene oxide feed.

Schmidt states at column 2, lines 50–55 that: "Propylene oxide, however, has a substantial solubility in water and is readily hydrolyzed to propylene glycol (PG) in the presence of large amounts of water"—i.e., in the reboiler section of the tower.

Meyer et al. U.S. Pat. No. 4,971,661 discloses the use of an aqueous acetone extraction to remove methanol from propylene oxide.

Meyer et al. point out that the presence of additional acetone (added to feed or solvent) serves as a buffer between the reboiler section and the balance of the tower. This is apparent if one looks at the normal boiling points (i.e., atmospheric pressure):

| Component | NBP (°C.) |
|---|---|
| Propylene Oxide (PO) | 34 |
| Acetone | 56 |
| Water | 100 |

The acetone serves as a buffer section in the tower between the PO and water (a high concentration of water is in the reboiler and a high concentration of PO is above the acetone buffer zone). The acetone buffer zone limits the contact of PO with a high concentration of water. It is apparent that the additional acetone makes its presence known in the reboiler as well as evidenced by lower reboiler temperatures. This also helps reduce PO to PG conversion as the reaction rate increases with increasing temperature. Any PO making its way to the reboiler will see a lower temperature, thus reducing its conversion to PG.

It is clear that the tower should be operated at as low a pressure as is practical to minimize PO loss.

c. Glycol and Glycol Ether Extractants

Washall U.S. Pat. No. 3,578,568 discloses a process for removing oxygen-containing impurities such as acetone, acetaldehyde and methanol from impure propylene oxide using a glycol such as ethylene glycol or propylene glycol as an extractive distillation agent. It is stated that the concentration of the solvent in the vapor space in the extractive distillation zone of the extractive distillation tower should preferably be between 15 and 50 mole percent of the total vapor.

Shih et al. U.S. Pat. No. 5,000,825 discloses the purification of monoepoxides such as propylene oxide that are contaminated with oxygenated impurities such as water, low molecular weight alcohols, low molecular weight ketones, low molecular weight aldehydes and the like by the extractive distillation of the contaminated monoepoxide using a lower glycol containing 2 to 4 carbon atoms. Examples of the lower glycols that are given in the patent include ethylene glycol, 1,2-propane diol, 1,3-propane diol, 1,4-butane diol, 1,2-butane diol, 1,3-butane diol, 1,4-butane diol, butane diol and 2,3-butane diol. It is stated that higher diols or higher glycol ethers do not provide sufficient selectivity for the removal of impurities and they are not included in the list of extractive distillation solvents suitable for use in the invention.

In Marquis et al. U.S. Pat. No. 5,139,622 the use of triethylene glycol is disclosed for the removal of methanol, acetone and water from propylene oxide contaminated with these impurities.

The use of dipropylene glycol as an extractive distillation agent for the removal of methanol, acetone and water from propylene oxide contaminated with these impurities is disclosed in Marquis et al. U.S. Pat. No. 5,160,587.

In copending and coassigned Peters et al. U.S. patent application Ser. No. 08/251,158, filed May 31, 1994 (D#81,307) now U.S. Pat. No. 5,464,505, and entitled "Use of Propylene Oxide Adducts in the Purification of Propylene Oxide by Extractive Distillation" the use of propylene oxide adducts of oxyethylene glycols as extractive distillation agents is disclosed.

In copending and coassigned Peters et al. U.S. patent application Ser. No. 08/251,151, filed May 31, 1994 (D#81,309), now U.S. Pat. No. 5,453,160, and entitled "Use of Mixed Polyoxypropylene Glycols in the Extractive Distillation of Propylene Oxide" the use of mixed polyoxypropylene glycols as extractive distillation agents is disclosed.

In copending coassigned Downs et al. U.S. patent application Ser. No. 08/378,291, filed Jan. 25, 1995 (D#81,316), and entitled "Controlled Continuous Purification of Propylene Oxide by Extractive Distillation", a process for the purification of acetone-contaminated propylene by extractive distillation is disclosed wherein an oxyalkylene glycol extractive distillation agent is used and wherein an acetone buffer zone is established and maintained in the distillation column to decrease the reaction of propylene oxide with water and with the oxyalkylene glycol extractive distillation agent.

SUMMARY OF THE INVENTION

In accordance with the present invention, an impure propylene oxide feedstock, such as a feedstock contaminated with 0.01 to 2 wt. % of water, from about 50 to about 4,000 ppm of methanol and containing from about 0.1 to about 2 wt. % of acetone, and more preferably about 0.4 to about 0.5 wt.% of acetone, is continuously charged to the lower half of an extractive distillation column containing at least about 10 theoretical plates and an oxyalkylene glycol extractive distillation agent is continuously charged to the tower at a point at least 4 stages above the impure propylene oxide feed point. Preferably, the extractive distillation tower will contain from about 30 to about 120 theoretical plates and the extractive distillation agent will be charged to the tower at a point of from 7 to 50 theoretical stages above the impure propylene oxide feed point. The extractive distillation agent is introduced into the extractive distillation column in the ratio of said feedstock to said extractive distillation agent of from about 1:1 to about 20:1, and more preferably 2:1 to 10:1, whereby a lower boiling (light) distillate fraction is continuously obtained consisting essentially of propylene oxide contaminated with trace amounts of water, methanol and acetone, such as about 5 to about 600 ppm of water, about 15 to 2,000 ppm of methanol and about 0.1 to about 100 ppm of acetone.

The extractive distillation conditions of temperature, pressure and acetone feed concentration should be correlated so as to establish an acetone buffer zone in the extractive distillation column at a point below the point of introduction of the impure feedstock. A higher boiling (heavier) distillation fraction containing substantially all of the oxyalkylene glycols, water, acetone and methanol introduced into said extractive distillation column is continuously withdrawn adjacent the bottom of the distillation column and passed to a first reboiler where it is heated at a temperature of about 90° to about 100° C. to partially vaporize the heavier distillation fraction to provide a first vaporized reboiler fraction rich in acetone and lean in oxyalkylene glycols. The unvaporized liquid portion of the higher boiling (heavier) distillation fraction is then passed to a second reboiler and heated therein at a temperature of about 180° to about 200° C. to provide further partial vaporization and a second vaporized reboiler fraction lean in acetone and rich in oxyalkylene glycols, and the first and said second vaporized recycle fractions are recycled to the extractive distillation column at a point below the acetone buffer zone.

BACKGROUND OF THE PRESENT INVENTION

When propylene is reacted in liquid phase with an organic hydroperoxide such as tertiary butyl hydroperoxide in solution in a solvent such as tertiary butyl alcohol in the presence of a soluble epoxidation catalyst such as a molybdenum epoxidation catalyst, a reaction mixture is formed comprising propylene oxide, an alcohol corresponding to the organic hydroperoxide feedstock and impurities including water and other oxygenated impurities such as methyl formate, acetaldehyde, acetone and methanol.

Propylene oxide is a hygroscopic substance, so that water is removed only with difficulty. It is important to remove as much of the water as possible, however, because the water present in the propylene oxide will tend to react with the propylene oxide to form propylene glycol.

It is also important to reduce the level of other oxygenated contaminants such as methanol and acetone to the lowest reasonably attainable level.

In accordance with conventional practice, an epoxidation reaction product formed by the molybdenum-catalyzed reaction of propylene oxide with tertiary butyl hydroperoxide in solution in tertiary butyl alcohol is separated into the principle components by distillation so as to form distillation fractions including a propylene distillation fraction, a propylene oxide distillation fraction, a tertiary butyl alcohol distillation fraction and a high boiling (heavy) distillation fraction containing the molybdenum catalyst and other products and by-products of the epoxidation reaction. However, the distillation fractions that are thus-obtained are characterized by the inclusion of impurities and, normally, must be further treated if commercially acceptable products are to be obtained. This is especially true for a propylene oxide distillation fraction contaminated with water and oxygenated contaminants including methanol and acetone.

As mentioned above, it has heretofore been proposed to use oxyalkylene glycols as extractive distillation agents in the continuous extractive distillation of an impure propylene oxide feedstock contaminated with water, methanol and acetone.

It has also been heretofore noted that if acetone is present in the feed or added to the column, an acetone buffer zone can form in the extractive distillation column above the reboiler and below the point of introduction of the impure feed. Thus, over a period of time (e.g., from about 5 to 24 hours of operation) the acetone charged to the extractive distillation column will tend to become concentrated at a point or zone in the column above the reboiler outlet line and the impure propylene oxide feed point, forming a detectable acetone buffer. Water concentration is comparatively high in the reboiler, where distillation temperatures are also the highest. As a consequence, there is a tendency for propylene glycol to form by the high temperature hydration of the propylene oxide and this represents a net loss of propylene oxide for the process. More importantly, under the mildly acidic conditions that prevail in the distillation column, propylene oxide can react with the oxyalkylene glycol extractive distillation agent to form a propylene oxide adduct. The adduct is effective as an extractive distillation agent, but also represents a net loss of propylene oxide.

The acetone buffer prevents the propylene oxide from propagating downward through the column toward the reboiler by altering vapor and liquid equilibrium conditions. Specifically, due to the higher boiling point of acetone relative to propylene oxide, the propylene oxide will preferentially fractionate to locations higher in the column than the acetone band. This prevents the propylene oxide from propagating to locations low in the column, specifically the column reboiler, where propylene oxide would be undesirably lost from the system.

The existence and location of the acetone buffer can be determined for a particular distillation column by running a temperature profile of the column to locate the point in the column where the distillation temperature approximates the boiling point of acetone at the pressure there prevailing, by taking and analyzing samples along the length of the column, etc.

I

In accordance with the present invention, an acetone buffer zone is maintained in the extractive distillation column by continuously withdrawing a higher boiling (heavier) distillation fraction containing substantially all of the oxyalkylene glycols, water, acetone and methanol from adjacent the bottom of the distillation column and passing it to a first reboiler and heating it therein at a temperature of about 90° to about 100° C. to partially vaporize the higher boiling (heavier) distillation fraction to provide a first vaporized reboiler fraction rich in acetone and lean in oxyalkylene glycols. The unvaporized liquid portion of the higher boiling (heavier) distillation fraction is passed to a second reboiler and heating therein at a temperature of about 180° to 200° C. to further partially vaporize the unvaporized liquid portion and to provide a second vaporized reboiler fraction lean in acetone and rich in oxyalkylene glycols. The first and said second vaporized fractions are recycled to the distillation column below the acetone buffer zone.

II

In accordance with a preferred embodiment of the present invention, a continuous extractive distillation process is provided for the distillation of an impure propylene oxide feedstock contaminated with water, methanol and acetone in an extractive distillation column containing at least 25 theoretical plates, and fitted with a pair of reboilers and a reflux condenser to remove oxygenated contaminants, the process including the steps of:

continuously introducing an impure propylene oxide feedstock contaminated with about 0.4 to about 1.5 wt. % of acetone into the lower half of an extractive distillation column, continuously introducing an oxyalkylene glycol extractive distillation agent having a molecular weight of not more than about 600 into the extractive distillation column at a point at least 4 theoretical plates above the point of introduction of the impure propylene oxide feedstock, the extractive distillation agent being introduced into the extractive distillation column in the ratio of feedstock to said extractive distillation agent of from about 1:1 to about 20:1, continuously maintaining distillation conditions including a pressure of about 10 to 40 psia, a reflux ratio of from about 1:1 to about 5:1 and a reboiler temperature within the range of about 100° to about 250° C. and a top temperature of about 20° to about 80° C. correlated to provide and maintain an acetone buffer zone in the distillation column below the point of introduction of the feedstock, continuously withdrawing a lower boiling (lighter) distillation fraction from the reflux condenser of said extractive distillation column consisting essentially of anhydrous propylene oxide contaminated with trace quantities of said acetone and methanol, continuously withdrawing a higher boiling (heavier) distillation fraction from adjacent the bottom of the extractive distillation column containing substantially all of the oxyalkylene glycols, water, acetone and methanol introduced into said extractive distillation column, passing the higher boiling (heavier) distillation fraction to a first reboiler and heating it therein at a temperature of about 90° to about 100° C. to partially vaporize the higher boiling (heavier) distillation fraction to provide a first vaporized reboiler fraction rich in acetone and lean in oxyalkylene glycols, passing the unvaporized liquid portion of the higher boiling (heavier) distillation fraction to a second reboiler and heating it therein at a temperature of about 180° to about 200° C. to further partially vaporize the unvaporized liquid portion to provide a second vaporized reboiler fraction lean in acetone and rich in oxyalkylene glycols, and recycling the first and said second vaporized recycle fractions to the extractive distillation column at a point below the buffer zone.

III

In accordance with another preferred embodiment of the present invention, a continuous extractive distillation process is provided for the distillation of an impure propylene oxide feedstock contaminated with water, methanol and acetone in an extractive distillation column containing at least 25 theoretical plates, and fitted with a pair of reboilers and a reflux condenser to remove oxygenated contaminants, including water the steps of:

continuously introducing an impure propylene oxide feedstock into the lower half of said extractive distillation column, the feedstock containing about 0.01 to about 2 wt. % of acetone, about 0.1 to about 2 wt. % of water and about 50 to 4000 ppm of methanol, continuously introducing an extractive distillation agent into the extractive distillation column at a point at least 4 theoretical plates above the point of introduction of the impure propylene oxide feedstock, the extractive distillation agent being introduced into the extractive distillation column in the ratio of feedstock to extractive distillation agent of from about 1:1 to about 20:1, continuously maintaining distillation conditions including a pressure of about 10 to 40 psia, a reflux ratio of from about 1:1 to about 5:1 and a reboiler temperature within the range of about 100° to about 250° C. and a top temperature of about 20° to about 80° C. correlated to provide and maintain an acetone buffer zone in the distillation column below the point of introduction of the feedstock, continuously withdrawing a lower boiling (lighter) distillation fraction from the reflux condenser of the extractive distillation column consisting essentially of anhydrous propylene oxide contaminated with trace quantities of acetone and methanol, continuously withdrawing a higher boiling (heavier) distillation fraction from adjacent the bottom of the extractive distillation column containing substantially all of the extractive distillation agent, water, acetone and methanol introduced into the extractive distillation column, passing the higher boiling (heavier) distillation fraction to a first reboiler and heating it therein at a temperature of about 90° to about 100° C. to partially vaporize the higher boiling (heavier) distillation fraction to provide a first vaporized reboiler fraction rich in acetone and lean in extractive distillation agent and a first unvaporized liquid fraction, passing the first unvaporized liquid fraction to a second reboiler and heating it therein at a temperature of about 180° to about 200° C. to further partially vaporize the first unvaporized liquid portion to provide a second vaporized reboiler fraction lean in acetone and rich in extractive distillation agent and a second unvaporized liquid fraction, recycling the first and said second vaporized recycle fractions to the extractive distillation column at a point below the acetone buffer zone, charging the second unvaporized liquid fraction to a separate distillation column and separating it therein into a lower boiling (lighter) distillation fraction comprising water, acetone and methanol and a higher boiling (heavier) extractive distillation fraction comprising the extractive distillation agent, and continuously recycling the higher boiling (heavier) extractive distillation agent distillation fraction to the extractive distillation column as the extractive distillation agent, the extractive distillation agent comprising triethylene glycol and a mixture of propylene oxide adducts of triethylene glycol formed in the extractive distillation column by the reaction of triethylene glycol with propylene oxide and having the formula:

wherein n is a positive integer having a value of 1 to about 4, m has a value of 3, and the mixture has an average molecular weight of about 250 to 350.

THE OXYALKYLENE GLYCOL EXTRACTIVE DISTILLATION AGENTS

In conducting the extractive distillation process of the present invention, any of the suitable known alkylene glycol extractive distillation agents can be used, such as propylene glycol, dipropylene glycol, tripropylene glycol, ethylene glycol, diethylene glycol, triethylene glycol, etc., or propylene oxide adducts thereof.

When propylene oxide is reacted with an oxyethylene glycol to provide a propylene oxide adduct of the oxyethylene glycol, the reaction product will actually comprise a mixture of isomers. For example, when one mole of propylene oxide is reacted with one mole of ethylene glycol, two isomers will be formed, as follows:

In like fashion, when two moles of propylene oxide react with ethylene oxide, an even more complex mixture of isomers is formed, i.e.:

In like fashion, when propylene oxide is reacted with propylene glycol to provide di-propylene glycol, the reaction product will actually comprise a mixture of isomers, as follows:

Thus, when propylene oxide reacts with dipropylene glycol to form tripropylene glycol, a mixture of isomeric tripropylene glycol isomers will be formed.

Accordingly, the mixture of polyoxypropylene glycols that may be used as extractive distillation agents in accordance with the present invention may be defined as a mixture having the formula:

wherein n and p are positive integers, m is a positive integer having a value of 1 to 3, the sum of n and p has a value of 1 to about 4, and the mixture having an average molecular weight of about 250 to 350.

When the extractive distillation process of the present invention is practiced on a continuous basis, the mixture of polyoxyalkylene glycols will be formed in situ by initially charging an oxyalkylene glycol such as ethylene glycol, diethylene glycol, triethylene glycol propylene glycol or dipropylene glycol to the extractive distillation tower. Thereafter, propoxylation of the initially charged oxyethylene glycol will occur, as described above and over the passage of time (e.g., about 100 hours of continuous operations) a mixture of polyoxypropylene glycols will be formed that will have the composition described above.

For example, about 0.1 to about 15 vol. % per hour of the total volume of circulating solvent may be removed and replaced with an equivalent volume of fresh solvent, a circulating stream of solvent can be obtained in which not more than about 5 to about 35 wt. % of the circulating stream of solvent will have a molecular weight of more than about 250.

During continuous operations of about 1,000 hours or more, and because of upsets in the extractive distillation column, the amount of higher boiling (heavier) propylene oxide adducts having molecular weights in excess of about 350 may increase to an extent such that the efficiency of the continuous extractive distillation operation deteriorates. When undesirably high levels of contaminants appear in the purified propylene oxide product, the problem can be solved by purging part of the circulating stream of extractive distillation agent from the system and replacing it with an equivalent volume of fresh oxyethylene glycol extractive distillation solvent.

Thus, when conducting continuous distillation operations in accordance with the preferred embodiment of the present invention, from about 0.1 to about 15 vol. % per hour of the total volume of circulating solvent is removed and replaced with an equivalent volume of fresh solvent, the amount being adjusted to provide a circulating stream of solvent having an average molecular weight of not more than about 350, such as an average molecular weight of about 250 to about 350.

DESCRIPTION OF THE PREFERRED EMBODIMENT

Figure 1:
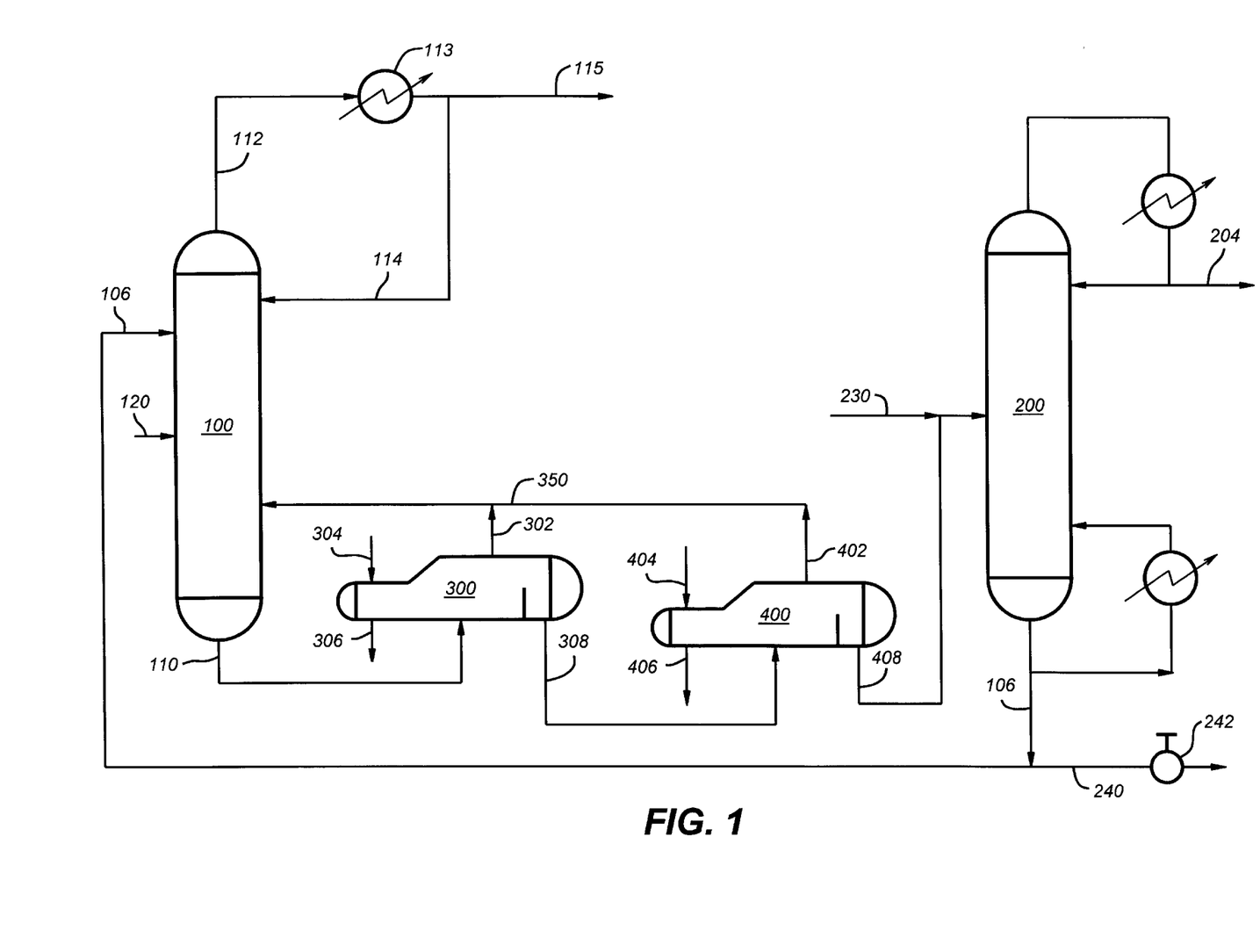
FIG. 1, is a schematic flow sheet with conventional parts omitted showing the general recovery sequence that is used in accordance with the present invention in purifying propylene oxide.

Turning now to the drawing, and especially to FIG. 1, there is shown a schematic flow sheet illustrating a preferred method of practicing the process of the present invention. In the drawing, conventional parts such as valves, pumps, temperature sensors, pressure sensors, heaters, coolers, flow control regulation apparatus, etc., have been omitted.

In accordance with a preferred embodiment of the present invention, propylene oxide is separated in a preliminary distillation zone (not shown) from other components of an epoxidation reaction mixture in order to provide an impure propylene oxide fraction contaminated with oxygen-containing impurities such as acetone, methanol, water, etc.

The impure propylene oxide feedstock that is thus obtained in the preliminary distillation zone is then purified in a propylene oxide purification distillation zone, which in accordance with the preferred embodiment of the present invention, comprises two distillation columns.

In accordance with the present invention, an impure propylene oxide feedstock fraction, such as a fraction contaminated with from about 50 to about 4,000 ppm of methanol, and containing from about 0.1 to about 2 wt. % of acetone (e.g., 0.4 to 1.5 wt. %) and about 0.01 to about 2 wt. % of water and other oxygen-containing impurities is charged by way of a line 120 leading to a distillation column 100 which, in accordance with the present invention, will preferably be a column containing at least about 10 theoretical plates, more preferably at least 25 theoretical plates and still more preferably, from about 30 to about 100 theoretical plates. The column 100 is suitably operated under distillation conditions including a pressure of about 10 to 40 psia, a reflux ratio of from about 2:1 to about 10:1, a reboiler temperature within the range of about 100° to about 250° C. (e.g., 210° C.) and a top temperature of about 20° to about 80° C. (e.g., about 20° C.).

The impure propylene oxide is preferably charged to the distillation column 100 in the lower half thereof. An extractive distillation agent comprising an oxyalkylene glycol is charged to the upper half of the distillation column 100 by an extractive distillation charge line 106.

A purified propylene oxide fraction, such as a fraction containing about 100 ppm or less of water, is removed from the column 100 as a lower boiling (lighter) distillation fraction 112, the purified propylene oxide in the line 112 containing significantly reduced amounts of methanol and acetone, such as about 15 to 900 ppm of methanol and about 0.01 to 100 ppm of acetone. A higher boiling (heavier) fraction 110 is withdrawn from the distillation column higher boiling (heavier) 100 which contains substantially all of the extractive distillation agent charged by the line 106 and also substantially all of the water, acetone and other oxygen-containing impurities introduced into the column 100 with the impure propylene oxide 120.

In accordance with the present invention, the higher boiling (heavier) distillation fraction 110 is charged to a first reboiler 300 and heated therein at a temperature of about 90° to about 100° C. to partially vaporize said higher boiling (heavier) distillation fraction to provide a first vaporized reboiler fraction that is rich in acetone and lean in oxyalkylene glycols, which is discharged from the reboiler 300 by a line 302. Energy for heating the higher boiling (heavier) distillation fraction 110 is supplied to the reboiler 300 in any suitable manner.

For example, low pressure steam, such as steam having a pressure of about 10 to 20 psia is charged by a steam charge line 304. Spent steam is removed from the reboiler 300 by a steam discharge line 306. The residence time of the higher boiling (heavier) distillation fraction 110 in the reboiler 300 should be regulated so as to as to permit about 50 vol. % to 70 vol. % of the distillation fraction 110 to vaporize for removal from the reboiler 300 by the line 302. The remaining liquid portion of the higher boiling (heavier) distillation fraction 110 is discharged from the first reboiler 300 as the first unvaporized liquid fraction 308.

In accordance with the present invention, the first unvaporized liquid fraction 308 is charged to a second reboiler 400 which is connected in series with the first reboiler 300, and heated therein at a temperature of about 180° to about 200° C. to partially vaporize said first unvaporized liquid fraction 308 to provide a second vaporized reboiler fraction rich in oxyalkylene glycols and lean in acetone, which is discharged from the reboiler 400 by a line 402. Energy for heating the first unvaporized liquid fraction 308 is supplied to the reboiler 400 in any suitable manner.

For example, high pressure steam, such as steam having a pressure of about 500 to about 650 psia is charged by a steam charge line 404. Spent steam is removed from the reboiler 400 by a steam discharge line 406. The residence time of the first unvaporized liquid fraction 308 in the reboiler 400 should be regulated so as to permit about 20 vol. % to 40 vol. % of the first unvaporized liquid fraction 308 to vaporize for removal from the reboiler 400 by the line 402. The remaining liquid portion of the first unvaporized liquid fraction 308 is discharged from the second reboiler 400 as a second unvaporized liquid fraction 408.

OPERATION

An impure propylene oxide feedstock having the composition given in Table 1 is charged by the line 120 to an extractive distillation column 100 containing about 100 theoretical trays.

TABLE I

Feed Compositions

| | Crude PO Feed (with Acetone) |
|---|---|
| Acetaldehyde (ppm) | 210 |
| Methanol (ppm) | 2200 |
| Methyl Formate (ppm) | 240 |
| Acetone (wt %) | 1.8 |
| t-butyl alcohol (ppm) | 1200 |
| water (ppm) | 1800 |

About 1,000 lbs./hr of triethylene glycol is charged by the line 106 adjacent the top of the tower 100. Distillation conditions are adjusted in the column 100 to provide for a top pressure of about 23 psia and a top temperature of about 115° F. and a bottom pressure of about 36 psia and a bottom temperature of about 185° F. About 32,000 lbs./hr of substantially pure propylene oxide is taken overhead by line 112 and liquified in condenser 113. About 22,000 lbs. per hour of the liquified propylene oxide is returned to the column 100 as reflux by the line 114 and the remaining 10,000 lbs./hr is discharged by the line 115.

About 26,000 lbs./hr of a higher boiling (heavier) distillation fraction is discharged from the distillation column 100 by the line 110. After being processed in a manner to be described, about 23,000 lbs./hr. is returned to the column 100 by the line 350 at a temperature of about 235° F. and about 3,000 lbs./hr is charged by line 408 to distillation column 200.

Under these conditions, an acetone buffer is formed in the distillation column 100 between the feed line 120 and the reboiler return line 350.

Figure 2:
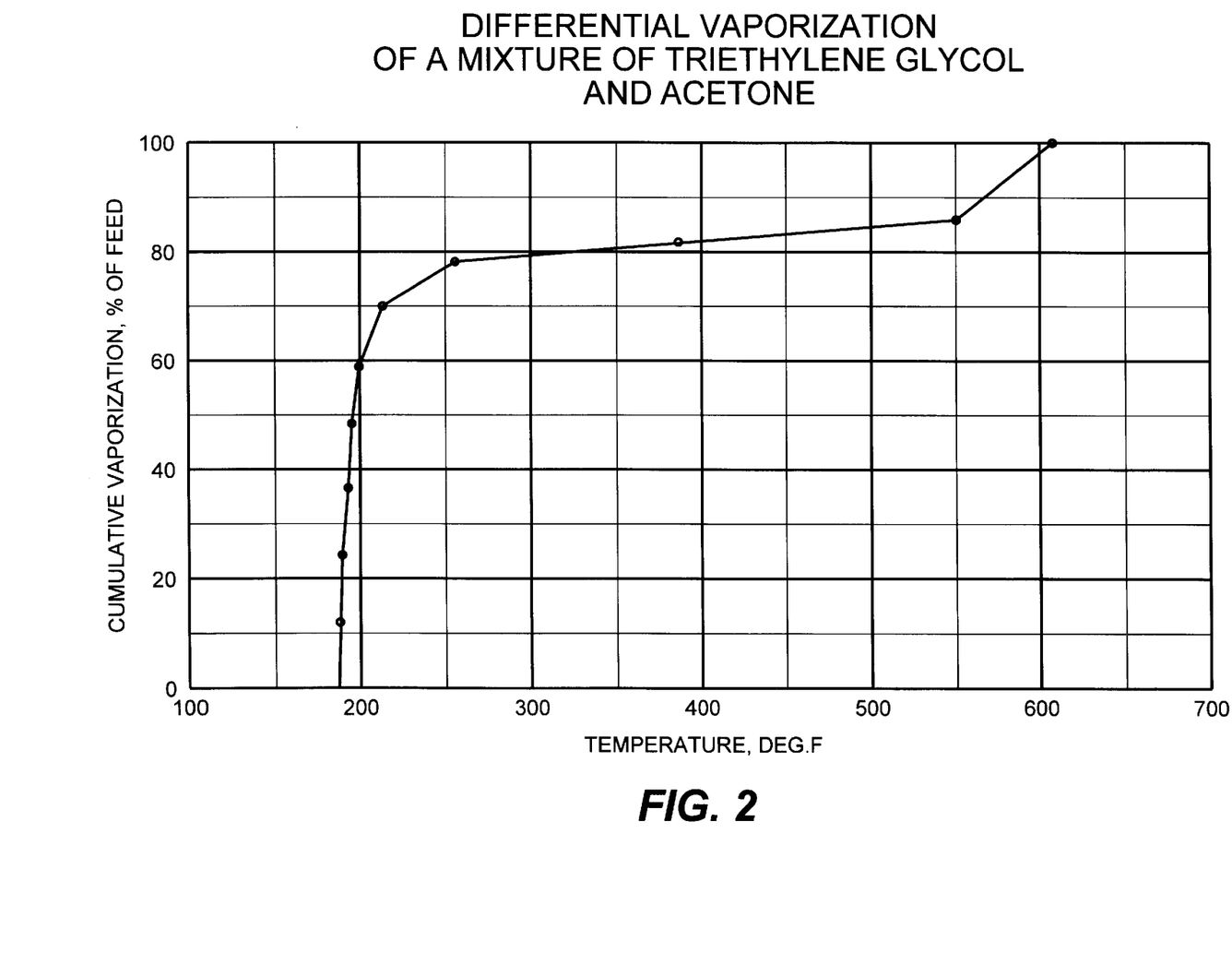
FIG. 2 is a chart showing the differential vaporization that occurs when a mixture of acetone and triethylene glycol is heated.

If the acetone buffer is to be maintained in the distillation column 100, it is important that substantially all of the acetone be returned to the distillation column 100 through the line 350. However, acetone has a boiling point of 56.2° C. (about 131° F.) while triethylene glycol has a boiling point of 287.4° C. (about 550° F.). Moreover, as shown by FIG. 2, is has been discovered in accordance with the present invention that the differential vaporization of a mixture of acetone with triethylene glycol changes as lower boiling acetone is stripped from the mixture. Thus, up to about 70 wt. % of the mixture will be vaporized at a temperature of about 170° F. to about 220° F. but temperatures of about 500° to about 570° F. are required to substantially complete the vaporization.

Therefore, if a single reboiler is used, and is operated at a temperature of about 170° F. to about 220° F., the acetone remaining in the unvaporized portion will be lost from the column.

However, through the provision of the second reboiler 400 connected in series with the first reboiler 300, the liquid removed from the first reboiler 300 by the line 308 can be efficiently heated to a temperature of about 180° to about 220° C. (about 350° to about 420° F.) with high quality steam, such as steam having a pressure of about 500# to about 650# psia. As a consequence, a second vapor fraction 402 is obtained that is rich in triethylene glycol and lean in acetone.

Returning now to FIG. 1, the 26,000 lbs./hr of heavy distillation fraction discharged from the distillation column 100 by the line 110 is charged to the first reboiler 300 where it is heated at a temperature of about 170° F. to about 220° F. About 20,000 lbs./hr of the fraction 110 is vaporized and discharged from the first reboiler by the line 302. The remaining 6,500 lbs./hr of the first liquid fraction 308 is charged to the second reboiler 400 where it is heated at a temperature of about 350° to about 420° F. An additional 3,000lbs./hr of the first liquid fraction 308 is vaporized and discharged from the second reboiler 400 by the line 402. The vapor in the line 302 and in the line 402 are charged to reboiler return line 350 so that about 23,000 lbs./hr of vapor is returned to the column 100 by the line 350 at a temperature of about 235° F.

The remaining 3,000 lbs./hr of the second liquid fraction 408 is charged to distillation column 200 where impurities such as methanol, acetone, water, etc., are removed overhead as a distillation fraction 204. The remainder, comprising substantially purified triethylene glycol is discharged by bottoms line 106 for recycle to the extractive distillation column 100.

The provision of the second reboiler 400 helps to improve the operation of the extractive distillation column 100. The second reboiler 400 provides just enough heat to boil the triethylene glycol while the first reboiler 300 provides the majority of the heat to run distillation column 100 (e.g., about 75% of the required heat duty). The flow of steam to the first reboiler 300 will adjust itself to keep the temperature profile positioned correctly in the column. For example, as the concentration of liquid triethylene glycol starts to rise in the first reboiler 300, the reboiler 300 starts to pinch off and less heat is added to the column 100. The smaller amount of heat addition then results in a drop in the concentration of triethylene glycol and allows the operation of the column 100 to return to normal.

During normal operations the flow of steam to the reboiler 300 is wide open so that the flow of steam is determined by the temperature difference between the steam temperature and the process temperature. The flow of steam to the reboiler 400 is then ratioed to the flow of steam to the reboiler 300, so that as the flow of steam to the reboiler 300 goes up, the flow of steam to the reboiler 400 will go up by a proportional amount.

The benefit of the present invention is obtained by promoting the formation and maintenance of an acetone buffer zone in the distillation column 100 below the feed line 120 and above the reboiler return line 350. If the acetone buffer zone starts to move down the extractive distillation column 100, the reboiler 300 will add more heat to the extractive distillation column 100 because of the increasing temperature difference between the lower bubble point of the liquid in the extractive distillation column 100 and the dew point of the steam charged to the reboiler 300 by the line 304. If the acetone buffer zone starts to migrate up the extractive distillation column 100, the reboiler 300 will add less heat as the temperature difference driving heat into the tower is pinched off by the increasing bubble point of the extractive distillation column 100 liquid. Hence, the present invention provides a self-stabilizing system for control of the acetone buffer zone in the extractive distillation column 100.

Having thus described our invention, what is claimed is:

1. A continuous operation of an extractive distillation column for the purification of a propylene oxide feedstock contaminated with water, methanol and acetone wherein said impure propylene oxide feedstock is continuously introduced into the lower half of said extractive distillation column under distillation conditions of pre-determined temperature and pressure which comprises the steps of : promoting the formation and maintenance of an acetone buffer zone in the distillation column below the point of introduction of said impure propylene oxide feedstock, wherein an oxyalkylene glycol extractive distillation agent is continuously introduced into said extractive distillation column above said buffer zone, wherein a lighter distillation fraction consisting essentially anhydrous propylene oxide contaminated with trace quantities of said acetone and methanol is continuously withdrawn from said extractive distillation column above the point at which said alkylene glycol extractive distillation agent is introduced, and wherein a heavier distillation fraction containing substantially all of the oxyalkylene glycols, water, acetone and methanol introduced into said extractive distillation column is continuously withdrawn adjacent the bottom of the distillation column, passing said heavier distillation fraction to a first reboiler and heating it therein at a temperature of about 90° to about 100° C. to partially vaporize said heavier distillation fraction to provide a first vaporized reboiler fraction rich in acetone and lean in oxyalkylene glycols, passing the unvaporized liquid portion of said heavier distillation fraction to a second reboiler connected in series with the first reboiler and heating it therein at a temperature of about 180° to about 220° C. to further partially vaporize said unvaporized liquid portion to provide a second vaporized reboiler fraction lean in acetone and rich in oxyalkylene glycols, and recycling said first and said second vaporized reboiler recycle fractions to said extractive distillation column at a point below said buffer zone.

2. An extractive distillation process as in claim 1 wherein the oxyalkylene glycol comprises triethylene glycol.

3. An extractive distillation process as in claim 2 wherein the second vaporized reboiler fraction is recycled to said extractive distillation column in an amount constituting about 10 to 20 wt. % of the amount of said first reboiler fraction recycled to said extractive distillation column.

4. An extractive distillation process as in claim 1 wherein the oxyalkylene glycol extractive distillation agent is a mixture of oxyalkylene glycols having molecular weights of not more than about 600.

5. An extractive distillation process as in claim 4 wherein the extractive distillation agent consists essentially of a mixture of propylene oxide adducts of oxyethylene glycols having the formula:

wherein n is a positive integer having a value of 1 to about 4, m is a positive integer having a value of 1 to 3 and the mixture has an average molecular weight of not more than about 600.

6. An extractive distillation process as in claim 5 wherein m has a value of 3.

7. A continuous extractive distillation process for the distillation of an impure propylene oxide feedstock contaminated with water, methanol and acetone in an extractive distillation column containing at least 25 theoretical plates, fitted with a pair of reboilers and a reflux condenser to remove oxygenated contaminants, including water, methanol and acetone from the impure propylene oxide which comprises the steps of:

continuously introducing said impure propylene oxide feedstock into the lower half of an extractive distillation column said feedstock containing about 0.4 to about 1.5 wt. % of acetone, continuously maintaining distillation conditions including a pressure of about 10 to 40 psia, a reflux ratio of from about 1:1 to about 5:1 and a reboiler temperature within the range of about 100° to about 250° C. and a top temperature of about 20° to about 80° C. correlated to provide and maintain an acetone buffer zone in said distillation column below the point of introduction of said feedstock, continuously introducing an oxyalkylene glycol extractive distillation agent having a molecular weight of not more than about 600 into said extractive distillation column at a point at least 4 theoretical plates above the point of introduction of said impure propylene oxide feedstock, said extractive distillation agent being introduced into said extractive distillation column in the ratio of feedstock to said extractive distillation agent of from about 1:1 to about 20:1, continuously withdrawing a lighter distillation fraction from the reflux condenser of said extractive distillation column consisting essentially of anhydrous propylene oxide contaminated with trace quantities of said acetone and methanol, continuously withdrawing a heavier distillation fraction from adjacent the bottom of said extractive distillation column containing substantially all of oxyalkylene glycols, water, acetone and methanol introduced into said extractive distillation column, passing said heavier distillation fraction to a first reboiler and heating it therein at a temperature of about 90° to about 100° C. with low pressure steam having a pressure of about 10 to about 20 psia to partially vaporize said heavier distillation fraction to provide a first vaporized reboiler fraction rich in acetone and lean in oxyalkylene glycols, passing the unvaporized liquid portion of said heavier distillation fraction to a second reboiler connected in series with said first reboiler and heating it therein at a temperature of about 180° to about 220° C. with high pressure steam having a pressure of about 500 to about 650 psia to further partially vaporize said unvaporized liquid portion to provide a second vaporized reboiler fraction lean in acetone and rich in oxyalkylene glycols, and recycling said first and said second vaporized reboiler recycle fractions to said extractive distillation column at a point below said buffer zone.

8. An extractive distillation process as in claim 7 wherein the oxyalkylene glycol comprises triethylene glycol.

9. An extractive distillation process as in claim 8 wherein the second vaporized reboiler fraction is recycled to said extractive distillation column in an amount constituting about 10 to 20 wt. % of the amount of said first reboiler fraction recycled to said extractive distillation column.

10. An extractive distillation process as in claim 7 wherein the oxyalkylene glycol extractive distillation agent is a mixture of oxyalkylene glycols having molecular weights of not more than about 600.

11. An extractive distillation process as in claim 10 wherein the extractive distillation agent consists essentially of a mixture of propylene oxide adducts of oxyethylene glycols having the formula:

wherein n is a positive integer having a value of 1 to about 4, m is a positive integer having a value of 1 to 3 and the mixture has an average molecular weight of not more than about 600.

12. An extractive distillation process as in claim 11 wherein m has a value of 3.

13. A continuous extractive distillation process for the continuous distillation of an impure propylene oxide feedstock contaminated with water, methanol and acetone and in an extractive distillation column containing at least 25 theoretical plates, fitted with a pair of reboilers and a reflux condenser to remove oxygenated contaminants, including water, methanol and acetone from the impure propylene oxide which comprises the steps of:

continuously introducing said impure propylene oxide feedstock into the lower half of said extractive distillation column, said feedstock containing about 0.4 to about 1.5 wt. % of acetone, continuously maintaining distillation conditions including a pressure of about 10 to 40 psia, a reflux ratio of from about 1:1 to about 5:1 and a reboiler temperature within the range of about 100° to about 250° C. and a top temperature of about 20° to about 80° C. correlated to provide and maintain an acetone buffer zone in said distillation column below the point of introduction of said feedstock, continuously introducing a triethylene glycol extractive distillation agent into said extractive distillation column at a point at least 4 theoretical plates above the point of introduction of said impure propylene oxide feedstock, said triethylene glycol being introduced into said extractive distillation column in the ratio of feedstock to triethylene glycol of from about 1:1 to about 20:1, continuously withdrawing a lighter distillation fraction from the reflux condenser of said extractive distillation column consisting essentially of anhydrous propylene oxide contaminated with trace quantities of said acetone and methanol, continuously withdrawing a heavier distillation fraction from adjacent the bottom of said extractive distillation column containing substantially all of triethylene glycol, water, acetone and methanol introduced into said extractive distillation column, passing said heavier distillation fraction to a first reboiler and heating it therein at a temperature of about 90° to about 100° C. to partially vaporize said heavier distillation fraction to provide a first vaporized reboiler fraction rich in acetone and lean in triethylene glycol and a first unvaporized liquid fraction, passing said first unvaporized liquid fraction to a second reboiler and heating it therein at a temperature of about 180° to about 220° C. to further partially vaporize said first unvaporized liquid portion to provide a second vaporized reboiler fraction lean in acetone and rich in triethylene glycol and a second unvaporized liquid fraction, recycling said first and said second vaporized reboiler recycle fractions to said extractive distillation column at a point below said buffer zone, charging said second unvaporized liquid fraction to a separate distillation column and separating therein into a lighter distillation fraction comprising water, acetone and methanol and a heavier distillation fraction comprising said triethylene glycol, and continuously recycling said heavier triethylene glycol distillation fraction to said extractive distillation column as said extractive distillation agent.

14. An extractive distillation process as in claim 13 wherein the second vaporized reboiler fraction is recycled to said extractive distillation column in an amount constituting about 10 to 20 wt. % of the amount of said first reboiler fraction recycled to said extractive distillation column.

15. A continuous extractive distillation process for the continuous distillation of an impure propylene oxide feedstock contaminated with water, methanol and acetone and in an extractive distillation column containing at least 25 theoretical plates, fitted with a pair of reboilers and a reflux condenser to remove oxygenated contaminants, including water, methanol and acetone from the impure propylene oxide which comprises the steps of:

continuously introducing said impure propylene oxide feedstock into the lower half of said extractive distillation column, said feedstock containing about 0.01 to about 2 wt. % of acetone, about 0.1 to about 2 wt. % of water and about 50 to 4000 ppm of methanol, continuously introducing an extractive distillation agent comprising triethylene glycol into said extractive distillation column at a point at least 4 theoretical plates above the point of introduction of said impure propylene oxide feedstock, said triethylene glycol being introduced into said extractive distillation column in the ratio of feedstock to triethylene glycol of from about 1:1 to about 20:1, continuously maintaining distillation conditions including a pressure of about 10 to 40 psia, a reflux ratio of from about 1:1 to about 5:1 and a reboiler temperature within the range of about 100° to about 250° C. and a top temperature of about 20° to about 80° C. correlated to provide and maintain an acetone buffer zone in said distillation column below the point of introduction of said feedstock, continuously withdrawing a lighter distillation fraction from the reflux condenser of said extractive distillation column consisting essentially of anhydrous propylene oxide contaminated with trace quantities of said acetone and methanol, continuously withdrawing a heavier distillation fraction from adjacent the bottom of said extractive distillation column containing substantially all of said extractive distillation agent, water, acetone and methanol introduced into said extractive distillation column, passing said heavier distillation fraction to a first reboiler and heating it therein at a temperature of about 90° to about 100° C. to partially vaporize said heavier distillation fraction to provide a first vaporized reboiler fraction rich in acetone and lean in extractive distillation agent and a first unvaporized liquid fraction, passing said first unvaporized liquid fraction to a second reboiler and heating it therein at a temperature of about 180° to about 220° C. to further partially vaporize said first unvaporized liquid portion to provide a second vaporized reboiler fraction lean in acetone and rich in extractive distillation agent and a second unvaporized liquid fraction, recycling said first and said second vaporized reboiler recycle fractions to said extractive distillation column at a point below said buffer zone, charging said second unvaporized liquid fraction to a separate distillation column and separating therein into a lighter distillation fraction comprising water, acetone and methanol and a heavier distillation fraction comprising said extractive distillation agent, and continuously recycling said heavier extractive distillation agent distillation fraction to said extractive distillation column as said extractive distillation agent, said extractive distillation agent comprising triethylene glycol and a mixture of propylene oxide adducts of triethylene glycol having the formula:

wherein n is a positive integer having a value of 1 to about 4, m has a value of 3 and the mixture has an average molecular weight of about 250 to 350.

16. An extractive distillation process as in claim 15 wherein the amount of second vaporized reboiler fraction recycled to said extractive distillation column constitutes about 10 to 20 wt. % of the amount of said first reboiler fraction recycled to said extractive distillation column.

* * * * *